United States Patent [19]

Lawrence

[11] 4,017,489

[45] Apr. 12, 1977

[54] PROCESS OF PREPARING UNSYMMETRICAL DISULFIDES

[75] Inventor: John P. Lawrence, Stow, Ohio

[73] Assignee: The Goodyear Tire & Rubber Company, Akron, Ohio

[22] Filed: July 10, 1975

[21] Appl. No.: 594,831

[52] U.S. Cl. .................. 260/243 B; 260/79.5 C; 260/79.5 P; 260/792; 260/793; 260/455 B; 260/246 B; 260/247.1 R; 260/247.1 B; 260/247.1 L; 260/293.55; 260/293.63; 260/293.85; 260/934

[51] Int. Cl.² ............ C07C 154/02; C07C 155/10; C07C 161/00; C07D 277/72

[58] Field of Search ..... 260/45.9 R, 455 B, 293.85, 260/79.5 C, 79.5 P, 792, 793, 247.1 R, 247.1 B, 247.1 L, 247.1 T, 306.5, 293.55, 293.63, 934, 293.58, 243 B, 246 B

[56] References Cited

UNITED STATES PATENTS

| | | |
|---|---|---|
| 2,747,005 | 5/1956 | Zerbe et al. ............... 260/246 B |
| 2,886,593 | 5/1959 | Louthan et al. ............. 260/793 |
| 2,891,059 | 6/1959 | Malz ........................ 260/247.1 |
| 2,965,535 | 12/1960 | Birum ...................... 260/793 |
| 3,544,531 | 12/1970 | Morita ..................... 260/784 |
| 3,847,880 | 11/1974 | Trivette et al. ............. 260/243 B |
| 3,872,062 | 3/1975 | Lawrence ................... 260/79.5 R |
| 3,899,460 | 8/1975 | Wilson ..................... 260/79.5 P |

*Primary Examiner*—V. P. Hoke
*Attorney, Agent, or Firm*—F. W. Brunner; J. A. Rozmajzl

[57] ABSTRACT

An N-(aminothio)-phthalimide such as N-(morpholinothio)-phthalimide is reacted with a compound having the structure RSH or a metallic salt thereof, for example, benzene thiol, to produce a compound having the structure $RSSNR^1R^2$, such as N-(phenyldithio)-morpholine. Compounds prepared according to this process are either accelerators or retarders.

2 Claims, No Drawings

PROCESS OF PREPARING UNSYMMETRICAL DISULFIDES

This invention relates to a process of preparing accelerators and retarders by reacting an imide with a thiol or metallic salt thereof. It also relates to a new class of accelerators.

The prior art teaches the preparation and use of various compounds as accelerators and retarders. Such art includes U.S. Pat. No. 3,539,538; Canadian Pat. No. 848,440; U.S. Pat. No. 2,888,445 and U.S. Pat. No. 3,086,018. Those skilled in the art are constantly searching for new types of accelerators as well as for new methods of preparing known retarders and accelerators.

It is an object of the present invention to provide a process of preparing accelerators and retarders. It is also an object of the present invention to provide a new class of accelerators. Other objects will become apparent as the description proceeds.

The objects of the present invention are accomplished by reacting a thiol compound having the structural formula RSA with an N-(aminothio)-amide having the following structural formula

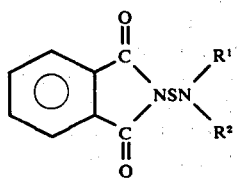

wherein A is selected from the group consisting of hydrogen, sodium and potassium, wherein R is selected from the group consisting of alykl radicals having 1 to 20 carbon atoms, cycloalkyl radicals having 6 to 12 carbon atoms, aralkyl radicals having 7 to 11 carbon atoms, aryl radicals having 6 to 10 carbon atoms and the radicals

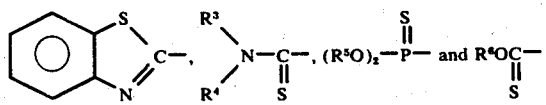

wherein $R^1$, $R^2$, $R^3$, $R^4$, $R^5$ and $R^6$ are selected from the group consisting of the alkyl, cycloalkyl and aralkyl radicals described for R. $R^5$ can also be an aryl radical having 6 to 10 carbon atoms. $R^1$ and $R^2$ and/or $R^3$ and $R^4$ can also be joined to form, with the attached nitrogen, a heterocyclic ring containing 5 to 7 carbon atoms which can contain, but need not contain, one other hetero atom selected from the group consisting of —O—, —S— and —N—. Specific heterocyclic rings include pyrrolidine, piperidine, morpholine and hexamethyleneimine, all of which are unsubstituted or substituted with one or two methyl radicals.

The reaction of the present method may be represented by the following.

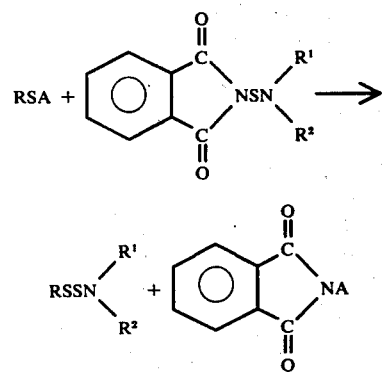

All of the products where R is an alkyl, cycloalkyl, aralkyl or aryl radical are retarders when used during the sulfur vulcanization of diene rubbers. All of the other products are accelerators used in the sulfur vulcanization of diene rubbers.

The term "aryl" as used herein denotes both substituted and unsubstituted aryl radicals. When substituted the radical contains one substituent selected from the group consisting of chloro, alkyl radicals containing 1 to 4 carbon atoms and alkyoxy radicals containing 1 to 4 carbon atoms.

The compounds prepared from thiols where R is

are accelerators. They are very unstable, however, and must be used immediately after their preparation.

The thiol compounds and metal salts thereof are all well known in the art.

The N-(aminothio)-imides are also well known in the art and are described, along with their preparation, in U.S. Pat. No. 3,872,062.

The imide reactants of the present invention are illustrated by, but not limited to, the following compounds.
  N-(dimethylaminothio)-phthalimide
  N-(diethylaminothio)-phthalimide
  N-(di-n-propylaminothio)-phthalimide
  N-(diisopropylaminothio)-phthalimide
  N-(di-n-butylaminothio)-phthalimide
  N-(diisobutylaminothio)-phthalimide
  N-(di-sec-butylaminothio)-phthalimide
  N-(N-methylcyclohexylaminothio)-phthalimide
  N-(dicyclohexylaminothio)-phthalimide
  N-(pyrrolidinothio)-phthalimide
  N-(piperidinothio)-phthalimide
  N-(hexamethyleniminothio)-phthalimide
  N-(morpholinothio)-phthalimide
  N-(N-ethylbenzylaminothio)-phthalimide
  N-(4-methylpiperidinothio)-phthalimide
  N-(2,6-dimethylmorpholinithio)-phthalimide
  N-(di-n-octylaminothio)-phthalimide The following compounds illustrate, but do not limit, the thiol reactants.
  methanethiol
  ethanethiol
  1-propanethiol
  2-propanethiol
  1-butanethiol 2-butanethiol
2-methyl-1-propanethiol
2-methyl-2-propanethiol
1-hexanethiol
1-octanethiol
1-dodecanethiol
cyclohexanethiol
cycloheptanethiol
cyclooctanethiol
a-toluenethiol
benzenethiol
p-toluenethiol
p-chlorobenzenethiol
p-methoxybenzenethiol
sodium dimethydithiocarbamate
sodium diethyldithiocarbamate
sodium di-n-butyldithiocarbamate
sodium N,N-pentamethylenedithiocarbamate
sodium N,N-oxydiethylenedithiocarbamate
O,O-dimethyl dithiophosphoric acid
O,O-diethyl dithiophosphoric acid
O,O-di-n-propyl dithiophosphoric acid
O,O-diisopropyl dithiophosphoric acid
O,O-di-n-butyl dithiophosphoric acid
O,O-di-n-hexyl dithiophosphoric acid
O,O-di-n-octyl dithiophosphoric acid
O,O-di-n-decyl dithiophosphoric acid
O,O-dicyclohexyl dithiophosphoric acid
O,O-diphenyl dithiophosphoric acid
O,O-di-p-tolyl dithiophosphoric acid
O,O-di-p-chlorophenyl dithiophosphoric acid
sodium O,O-diisopropyl dithiophosphate
potassium O,O-diisopropyl dithiophosphate
potassium methyl xanthate
potassium ethyl xanthate
sodium ethyl xanthate
potassium n-propyl xanthate
potassium isopropyl xanthate
potassium n-butyl xanthate
potassium sec.butyl xanthate
potassium isobutyl xanthate
potassium n-hexyl xanthate
potassium n-octyl xanthate
potassium n-decyl xanthate
potassium cyclohexyl xanthate
potassium benzyl xanthate The products of the process of the present invention are illustrated by, but not limited to, the following compounds as well as the compounds described in, and subsequent to, the working examples.

N-(cyclohexyldithio)-morpholine
N-(phenyldithio)-morpholine
N-(p-chlorophenyldithio)-morpholine
N-(benzyldithio)-morpholine
N-(1-hexyldithio)-morpholine
N-(1-dodecyldithio)-piperidine
N-(2-propyldithio)-diisopropylamine
N-(1-butyldithio)-dicyclohexylamine
N-(O,O-diisopropyl thiophosphoryldithio)-piperidine
N-(O,O-diisopropyl thiophosphoryldithio)-diisopropylamine
N-(O,O-diisopropyl thiophosphoryldithio)-dicyclohexylamine
N-(O,O-dimethyl thiophosphoryldithio)-N-ethylbenzylamine
N-(O,O-dicyclohexyl thiophosphoryldithio)-morpholine
N-(O,O-diethyl thiophosphoryldithio)-di-n-octylamine
N-(O,O-diphenyl thiophosphoryldithio)-N-methylcyclohexylamine
N,N-dimethyl-S-(morpholinothio)-dithiocarbamate
N,N-dimethyl-S-(diisopropylaminothio)-dithiocarbamate
N,N-dimethyl-S-(dicyclohexylaminothio)-dithiocarbamate
N,N-dimethyl-S-(N-ethylbenzylaminothio)-dithiocarbamate
N,N-dimethyl-S-(dimethylaminothio)-dithiocarbamate
N,N-pentamethylene-S-(morpholinothio)-dithiocarbamate
N,N-oxydiethylene-S-(morpholinothio)-dithiocarbamate
O-ethyl-S-(piperidinothio)-dithiocarbonate
O-ethyl-S-(diisopropylaminothio)-dithiocarbonate
O-ethyl-S-(dicyclohexylaminothio)-dithiocarbonate
O-ethyl-S-(N-ethylbenzylaminothio)-dithiocarbonate
O-isopropyl-S-(morpholinothio)-dithiocarbonate
O-isobutyl-S-(morpholinothio)-dithiocarbonate
O-n-propyl-S-(morpholinothio)-dithiocarbonate
O-sec-butyl-S-(morpholinothio)-dithiocarbonate
O-methyl-S-(morpholinothio)-dithiocarbonate
O-n-butyl-S-(morpholinothio)-dithiocarbonate
O-cyclohexyl-S-(morpholinothio)- dithiocarbonate
O-n-octyl-S-(morpholinothio)-dithiocarbonate
O-benzyl-S-(morpholinothio)-dithiocarbonate
2-(morpholinodithio)-benzothiazole
2-(piperidinodithio)-benzothiazole
2-(dimethylaminodithio)-benzothiazole
2-(diethylaminodithio)-benzothiazole
2-(diisopropylaminodithio)-benzothiazole
2-(ethylbenzylaminodithio)-benzothiazole
2-(di-n-butylaminodithio)-benzothiazole
2-(N-methylcyclohexylaminodithio)-benzothiazole
2-(2,6-dimethylmorpholinodithio)-benzothiazole The method of the present invention does not require a catalyst and no advantage is gained by operating at pressures higher or lower than atmospheric. Any organic solvent can be used for the reactants. For example, hydrocarbons such as hexane, heptane, benzene, toluene and xylene can be used. Alcohols such as methanol, ethanol, and 2-propanol as well as ethers such as diethyl ether, tetrahydrofuran and dioxane can be used as well as chlorinated hydrocarbons such as dichloromethane, chloroform, carbon tetrachloride and chlorobenzene. Ketones can also be used, for example, acetone, 2-butanone and 3-pentanone. Generally a hydrocarbon solvent is preferred for preparing compounds of classes I, II and IV. Generally an alcohol solvent is preferred for preparing compounds of classes III and V.

When producing a chemical product it is desirable that the conditions of the process be as mild as possible in order to minimize side reactions which lead to the formation of undesirable by-products. It is also desirable, when more than one product is formed during the normal course of a chemical reaction, that the products be easily separable on the basis of differences in solubility in the reaction medium. Furthermore, in order to make the process as economical as possible, it is desirable to utilize all of the products of a chemical reaction such as by recycling a normal by-product to make additional starting material.

The present process, when conducted within the temperature limits specified, has been found to be very selective in nature affording a mixed disulfide and phthalimide or a salt of phthalimide. The two products are readily separable on the basis of solubility. Reactions in which free phthalimide are formed, that is when A=H, are preferably conducted in a hydrocarbon solvent in which the phthalimide is largely insoluble and the mixed disulfide soluble. Reactions in which a metal salt of phthalimide is formed, that is when A = metal ion, are preferably conducted in an alcohol solvent since on dilution with water the phthalimide salt dissolves and the mixed disulfide remains undissolved. Pure phthalimide can be recovered from these processes and recycled to prepare additional starting N-(aminothio)-phthalimide.

Reaction temperatures can vary between 0° C. and 150° C. The temperature range between 10° C. and 30° C. is preferred when employing a metal salt of a thiol, i.e., when A is a metal ion. Temperatures in the range from 25° C. to 120° C. are preferred when the free thiol is used, i.e., when A is hydrogen.

The molar ratio of reactants may vary from 5:1 to 1:5 without affecting the outcome of the reaction. However, no advantage is obtained using any ratio other than 1:1 since excess reactants merely complicate ths isolation of the product.

Examples 1 to 5 illustrate, but are not intended to limit, the process of the present invention.

EXAMPLE 1

N-(N-ethylbenzylaminothio)-phthalimide (6.24 grams, 20 millimoles) was stirred in 100 milliliters of benzene and 2.2 grams (20 millimoles) of benzenethiol was added. The mixture was refluxed one hour, then cooled to room temperature and filtered to remove phthalimide. The filtrate was washed with 10 percent NaOH, then with water, dried (Na$_2$SO$_4$) and concentrated under reduced pressure to afford 5.2 grams (94.5%) of N-(phenyldithio)-N-ethylbenzylamine as a pale yellow liquid.

Other compounds which were prepared by this method are listed below.
  N-(cyclohexyldithio)-morpholine
  N-(phenyldithio)-morpholine
  N-(p-chlorrophenyldithio)-morpholine
  N-(benzyldithio)-morpholine
  N-(1-hexyldithio)morpholine
  1,2-bis(morpholinodithio)-ethane (m.p. 97–99° C.)
  N-(1-dodecyldithio)-piperidine
  N-(2-propyldithio)-diisopropylamine
  N-(1-butyldithio)-dicyclohexylamine
  All but the ethane compound were liquids.

EXAMPLE 2

N-(dicyclohexylaminothio)-phthalimide (7.16 grams, 20 millimoles) was stirred in 100 milliliters of benzene and 3.34 grams (20 millimoles) of 2-mercaptobenzothiazole was added. The mixture was refluxed one hour, then cooled to room temperature and filtered to remove phthalimide. The filtrate was concentrated under reduced pressure to afford a liquid residue (7.1 grams, 93.8%). This was dissolved in petroleum ether and scratched with a glass rod to induce crystallization. After crystallization was complete, the crystals were filtered and recrystallized from 2-propanol to afford pure 2-(dicyclohexylaminodithio)-benzothiazole which had a melting point of 84°–86° C.

Listed below are other benzothiazoles which were prepared by this method.

|  | Melting Point° C. |
|---|---|
| 2-(morpholinodithio)-benzothiazole | 130.5 – 132 |
| 2-(diisopropylaminodithio)-benzothiazole | 63 – 64 |
| 2-(N-ethylbenzylaminodithio)-benzothiazole | liquid |
| 2-(piperidinodithio)-benzothiazole | 85 – 86 |

EXAMPLE 3

N-(piperidinothio)-phthalimide (13.1 grams, 50 millimoles) were stirred in 250 milliliters of ethanol at room temperature and 7.2 grams (50 millimoles of sodium dimethyldithiocarbamate were added in one portion. The resulting mixture was stirred one-half hour at room temperature and then poured into 1200 milliliters of water. The precipitated product was filtered, washed with water, and dried at 60° C. Recrystallization from ethanol gave 10.7 grams (90.7%) of N,N-dimethyl-S-(piperidinothio)-dithiocarbamate with a melting point of 86°–87.5° C.

Listed below are other carbamates which were prepared by this method.

|  | Melting Point° C. |
|---|---|
| N,N-dimethyl-S-(morpholinothio)-dithiocarbamate | 98 – 100 |
| N,N-dimethyl-S-(diisopropylaminothio)-dithiocarbamate | 42 – 44 |
| N,N-dimethyl-S-(dicyclohexylaminothio)-dithiocarbamate | 93 – 95 |
| N,N-dimethyl-S-(N-ethylbenzylaminothio)-dithiocarbamate | 44 – 45.5 |
| N,N-oxydiethylene-S-(morpholinothio)-dithiocarbamate | 122 – 123 |

EXAMPLE 4

N-(morpholinothio)-phthalimide (13.2 grams, 50 millimoles) was stirred in 100 milliliters of benzene. The mixture was heated to reflux and 10.7 grams (50 millimoles) of O,O-diisopropyl dithiophosphoric acid was added gradually. After one hour at reflux, the mixture was cooled to room temperature and filtered to remove 7.4 grams (100%) of phthalimide with a melting point of 234°–235° C. The filtrate was concentrated under reduced pressure to afford 14.7 grams (88.9%) N-(O,O-diisopropyl thiophosphoryldithio)-morpholine as a pale yellow liquid.

Listed below are other compounds which were prepared by this method.
  N-(O,O-diisopropyl thiophosphoryldithio)-piperidine
  N-(O,O-diisopropyl thiophosphoryldithio)-diisopropylamine
  N-(O,O-diisopropyl thiophosphoryldithio)-dicyclohexylamine
  N-(O,O-dimethyl thiophosphoryldithio)-N-ethylbenzylamine
  N-O,O-dicyclohexyl thiophosphoryldithio)-morpholine
  All of the products were liquids.

EXAMPLE 5

N-(morpholinothio)-phthalimide (13.2 grams, 50 millimoles) was stirred in 250 milliliters of ethanol and 8.0 grams (50 millimoles) of potassium ethyl xanthate was added. The resulting mixture was stirred 30 minutes at room temperature and then poured into one liter of water. The oily product was extracted into hexane, the extract dried ($Na_2SO_4$), and concentrated in vacuo to afford 11.1 grams (92.2%) of pure O-ethyl-S-(morpholinothio)-dithiocarbonate as a pale yellow liquid.

Listed below are other S-(aminothio)-dithiocarbonates which were prepared by this procedure.
- O-isopropyl-S-(morpholinothio)-dithiocarbonate
- O-isobutyl-S-(morpholinothio)-dithiocarbonate
- O-n-propyl-S-(morpholinothio)-dithiocarbonate
- O-sec-butyl-S-(morpholinothio)-dithiocarbonate
- O-methyl-S-(morpholinothio)-dithiocarbonate (Melting point 51°–52° C.)
- O-n-butyl-S-(morpholinothio)-dithiocarbonate
- O-cyclohexyl-S-(morpholinothio)-dithiocarbonate
- O-n-octyl-S-(morpholinothio)-dithiocarbonate
- O-benzyl-S-(morpholinothio)-dithiocarbonate
- O-ethyl-S-(piperidinothio)-dithiocarbonate
- O-ethyl-S-(diisopropylaminothio)-dithiocarbonate
- O-ethyl-S-(dicyclohexylaminothio)-dithiocarbonate
- O-ethyl-S-(N-ethylbenzylaminothio)-dithiocarbonate All but the O-methyl compound were liquids.

The following illustrate the use of sulfenyl thiocarbonates of Example 5 as vulcanization accelerators. A natural rubber masterbatch of the following formulation was used.

|  | Parts by Weight |
| --- | --- |
| Smoked sheet | 100.0 |
| HAF black | 50.0 |
| Stearic acid | 3.0 |
| Softener | 3.0 |
| Zinc oxide | 3.0 |
| Amine antioxidant | 1.0 |
| Sulfur | 2.5 |
|  | 162.5 |

EXAMPLE 6

Rubber mixes of the following composition were compounded on a rubber mixing mill and vulcanized at 135° C. The sulfenyl thiocarbonates were compounded at the 0.75 part level. As a control, 0.5 part of 2-(morpholinodithio)-benzothiazole was used in Mix No. 1.

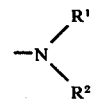

TABLE

| Mix. No. | 1 | 2 | 3 | 4 | 5 | 6 |
| --- | --- | --- | --- | --- | --- | --- |
| –N(R¹)(R²) | — | Morpholino | Piperidino | Diisopropyl-amino | Dicyclohexyl-amino | N-ethyl-benzylamino |
| Mooney Scorch at 135° C. (mins. to minimum + 5 value) | 13.3 | 12.8 | 10.4 | 11.7 | 10.8 | 10.9 |
| Vulcanization time at 135° C. (mins.) | 55.3 | 46.1 | 46.1 | 92.7 | 96.5 | 66.3 |
| Tensile strength (Kg/cm²) | 275.4 | 269.3 | 269.3 | 240.7 | 212.2 | 263.2 |
| Elongation at break (percent) | 525 | 520 | 470 | 540 | 530 | 505 |
| Modulus at 300% elong. (Kg/cm²) | 144.8 | 142.8 | 163.2 | 114.2 | 98.9 | 139.7 |

The data in the table demonstrate that all of the compounds tested were vulcanization accelerators. Had no accelerator been used, the vulcanization times would have been several hundred minutes. The Mooney scorch values indicate that the compounds also impart good processing safety.

Various analogs of the compound used in Mix No. 2 were evaluated and found to accelerate the rate of vulcanization, having vulcanization times of from 37.9 minutes to 91.0 minutes. The control using 2-(morpholinodithio)-benzothiazole had a vulcanization time of 47.7 minutes. Scorch times were from 11.5 to 12.8 minutes, the control having a value of 12.5 minutes. The analogs differed in their R radical. The R radicals of the compounds tested were isopropyl, n-propyl, isobutyl, 2-butyl, n-butyl, cyclohexyl and n-octyl.

While certain representative embodiments and details have been shown for the purpose of illustrating the invention, it will be apparent to those skilled in this art that various changes and modifications may be made therein without departing from the spirit or scope of the invention.

What is claimed is:

1. A process of preparing a compound having the structure

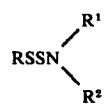

comprising reacting a thiol compound having the structure

RSA with an N-(aminothio)-imide having the structure

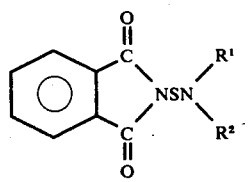

wherein A is selected from the group consisting of hydrogen, sodium and potassium, wherein R is selected from the group consisting of alkyl radicals having 1 to 20 carbon atoms, cycloalkyl radicals having 6 to 12 carbon atoms, aralkyl radicals having 7 to 11 carbon atoms, aryl radicals having 6 to 10 carbon atoms and the radicals

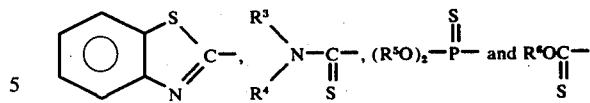

wherein $R^1$, $R^2$, $R^3$, $R^4$, $R^5$ and $R^6$ are selected from the group consisting of the alkyl, cycloalkyl and aralkyl radicals described for R and wherein $R^5$ can also be an aryl radical having 6 to 10 carbon atoms and wherein $R^1$ and $R^2$ and/or $R^3$ and $R^4$ can also be joined to form, with the attached nitrogen, a heterocyclic ring containing 5 to 7 carbon atoms which can contain, but need not contain, one other hetero atom selected from the group consisting of —O—, —S— and —N—.

2. The process according to claim 1 wherein the N-(aminothio)-imide is N-(morpholinothio) phthalimide.

* * * * *